United States Patent [19]
Plotkin

[11] Patent Number: 5,820,579
[45] Date of Patent: Oct. 13, 1998

[54] METHOD AND APPARATUS FOR CREATING PULSATILE FLOW IN A CARDIOPULMONARY BYPASS CIRCUIT

[75] Inventor: Neil D. Plotkin, Pasadena, Calif.

[73] Assignee: Medtronic, Inc., Minneapolis, Minn.

[21] Appl. No.: 644,635

[22] Filed: Apr. 30, 1996

[51] Int. Cl.⁶ ............................................. A61M 37/00
[52] U.S. Cl. ........................ 604/5; 128/DIG. 3; 422/44
[58] Field of Search ................... 604/4–6; 128/DIG. 3; 422/44, 45

[56] References Cited

U.S. PATENT DOCUMENTS

| | | | |
|---|---|---|---|
| 3,877,843 | 4/1975 | Fischel | 417/394 |
| 4,529,397 | 7/1985 | Hennemuth et al. | 604/4 |
| 4,540,399 | 9/1985 | Litzie et al. | 604/4 |
| 4,598,697 | 7/1986 | Numazawa et al. | 604/4 |
| 4,610,656 | 9/1986 | Mortensen . | |
| 4,627,419 | 12/1986 | Hills | 604/4 |
| 4,828,543 | 5/1989 | Weiss et al. | 604/4 |
| 5,069,661 | 12/1991 | Trudell | 604/4 |
| 5,141,847 | 8/1992 | Sugimachi et al. . | |
| 5,186,431 | 2/1993 | Tamari | 604/4 |
| 5,270,005 | 12/1993 | Raible | 604/4 |
| 5,385,540 | 1/1995 | Abbott et al. | 604/4 |
| 5,429,595 | 7/1995 | Wright, Jr. et al. | 604/4 |

FOREIGN PATENT DOCUMENTS

| | | |
|---|---|---|
| 0309642A1 | 9/1981 | European Pat. Off. . |
| 0654276A1 | 11/1993 | European Pat. Off. . |
| 4451277 | 7/1966 | France . |

*Primary Examiner*—John G. Weiss
*Assistant Examiner*—Ki Yong O
*Attorney, Agent, or Firm*—Harry G. Weissenberger

[57] ABSTRACT

Pulsatile cardiopulmonary flow closely approximating a natural heartbeat is generated in a heart-lung machine by using a proportioning valve to partly convey blood in the machine's cardiopulmonary circuit to the arterial supply line, and to partly recycle that blood into the cardiopulmonary circuit upstream of the arterial pump. The relative proportions of conveying and recycling are varied in accordance with a waveform approximating the waveform of a human heartbeat.

10 Claims, 2 Drawing Sheets

METHOD AND APPARATUS FOR CREATING PULSATILE FLOW IN A CARDIOPULMONARY BYPASS CIRCUIT

FIELD OF THE INVENTION

This invention relates to heart-lung machines, and more particularly to a method and apparatus for simulating the natural heartbeat's pressure pattern in the blood output of the heart-lung machine.

BACKGROUND OF THE INVENTION

The natural human heart provides the body with a pulsatile flow of blood corresponding to the filling and emptying (beating) of the various chambers of the heart. The instantaneous blood flow rate varies in a complex cyclical manner from near zero to some maximum rate, with the overall blood flow rate being a time weighted average.

The cardiopulmonary bypass circuits of heart-lung machines used in open-heart surgery typically utilize centrifugal or positive displacement (i.e. roller type) pumps to provide the motive power for circulation of the blood. These pumps provide an essentially constant flow rate of blood through the circuit at all times, the instantaneous rate and the average rate being nearly identical.

Medical studies have suggested that pulsatile flow, being more physiologically correct than constant flow, may have a beneficial impact on the efficacy of the extracorporeal perfusion. This can result in improved patient outcomes following cardiac bypass surgery.

Various ways have been proposed to mimic in a heart-lung machine the natural pulsatile flow of the heart, but none of them have so far been satisfactory. The simplest way of providing a pulsed flow is to cyclically clamp and unclamp the inlet or outlet line of the heart-lung machine's arterial pump. Clamping the pump inlet is not desirable since it can create very high suction pressures in the inlet which can damage the red blood cells, or in some cases even cause cavitation which can potentially release gas bubbles into the blood stream. Further, during the low flow or rest periods, the pump rotors spin on a stagnant volume of fluid, which may result in mechanical trauma to the blood cells. Clamping the pump outlet is not desirable in a centrifugal pump due to this mechanical trauma. Clamping the pump outlet is not desirable in a positive displacement pump since the rapid buildup of pressure in the lines can rupture the connections or tubing, potentially resulting in a catastrophic event.

A more acceptable way of creating pulsatile flow is to vary the speed of the pump in a cyclical manner. This is easily accomplished electronically by the pump controller. However, the inertia of the spinning elements of the pump tends to render the resulting waveform more sinusoidal than the natural heartbeat waveform and forces the wave period to be longer than the natural period. In addition, the components of the bypass circuit downstream of the pump, such as the oxygenator and arterial filter, also damp the pulses due to their volumetric holdup.

Lastly, a reciprocating type pump such a a diaphragm or bladder pump can be employed to create pulses in the flow. These pumps tend to be more mechanically complex than the roller or centrifugal types and do not lend themselves to either easy cleaning, sanitation, and sterilization for reuse, or low cost manufacture for one-time disposable use. Increased blood trauma is experienced in these pumps due to the multiple check valves in the flow path and stagnant areas due to less than perfect chamber filling and ejection. Lastly, as mentioned above, downstream components still damp the pulses and thus reduce the beneficial effects of the reciprocating pump.

SUMMARY OF THE INVENTION

The present invention provides an undamped pulsatile blood output in a heart-lung machine that is a very close approximation of the pulsation of the human heart by placing an automatic proportioning valve downstream of the oxygenator, filter, and other components in the cardiopulmonary circuit of the heart-lung machine. Pulsatile flow is achieved by cyclically switching the blood flow between the arterial supply line and a recycle line which returns the blood to a point upstream of the arterial pump. This eliminates the damping effect of the various components in the bypass circuit. Since a proportioning valve only redirects flow and never actually stops it, the device can be used with both positive displacement and centrifugal pumps without fear of cavitation, overpressurization, stagnation, excessive blood trauma or shear heating.

The inventive system consists of a single use (i.e. disposable) plastic proportioning valve connected to a reusable electric or pneumatic actuator and control console. Additional inputs to the console can be from a flow meter, pump speed controller, air-in-line detector or other external signal.

The inventive valve can be sterilized and supplied either pre-connected into the bypass circuit or as a stand alone component which may be inserted into the circuit in the field. Although traditional plug type proportioning valves are acceptable, a low pressure drop, low shear valve design such as a diaphragm type valve, produced from biocompatible materials, is preferred since this will minimize any mechanical trauma to the blood.

The function of the controller is to provide the user interface to set the periodicity, amplitude, and waveform of the pulses and to send appropriate control signals based on the setpoints to the valve actuator to effect the pulsatile flow. If desired, the controller can utilize the additional inputs mentioned above to perform additional control functions.

Periodicity of the pulses is controlled by the rate of valve cycling and can be set by the user. Since the inertia of the valve stem is relatively small, rapid cycling of the valve is easily accomplished. This is a clear advantage over systems utilizing pump speed as the means of effecting pulsatile flow. If capability for external triggering is built into the controller, the patient's own heartbeat can be used to pace or set the cycling of the valve. This would be useful at the end of the surgical procedure to aid in weaning the patient from the heart-lung machine.

The waveform of the pulses is controlled by the rate of change of the position of the proportioning mechanism which can be set by the user. Slow movement will create a sinusoidal waveform, rapid movement will create a square waveform, and complex movement patterns can create waveforms nearly identical to the human pulse. The ability to create any waveform is a clear advantage over the prior art systems which utilize occlusive clamps or pulsatile pumps to create the pulsatile flow.

The amplitude of the pulses is controlled by the relative proportion of the total flow through the supply line. This can vary from no flow (100% recycle) to full flow (100% supply), or any combination in between. This parameter can be set by the user.

If an air-in-line detector is placed an appropriate distance upstream of the valve, the system can act as an automatic air eliminator. When air is detected, the valve can go into 100% recycle mode which will divert the air back upstream where it will be eliminated through the oxygenator or caught in the bubble trap on the arterial filter. The diversion time can be pre-set to some value, or the valve may remain in recycle mode until manually switched back into the pulse mode.

An averaging flow meter is preferably placed downstream of the valve to provide information regarding the actual flow rate to the patient. The averaging function is necessary due to the fluctuations in flow rate caused by the pulsing flow. The controller can readily be configured to provide feedback to the arterial pump to maintain a desired average flow rate.

Another benefit of the inventive system is that due to the recycle loop, the average residence time of the blood in the oxygenator is increased. This increases the likelihood that the blood will be completely oxygenated before being transferred back to the patient. In addition, the recycled blood helps to pre-cool or pre-heat the incoming blood, which reduces the load on the heat exchanger in the oxygenator.

DESCRIPTION OF THE PREFERRED EMBODIMENT

Figure 1:
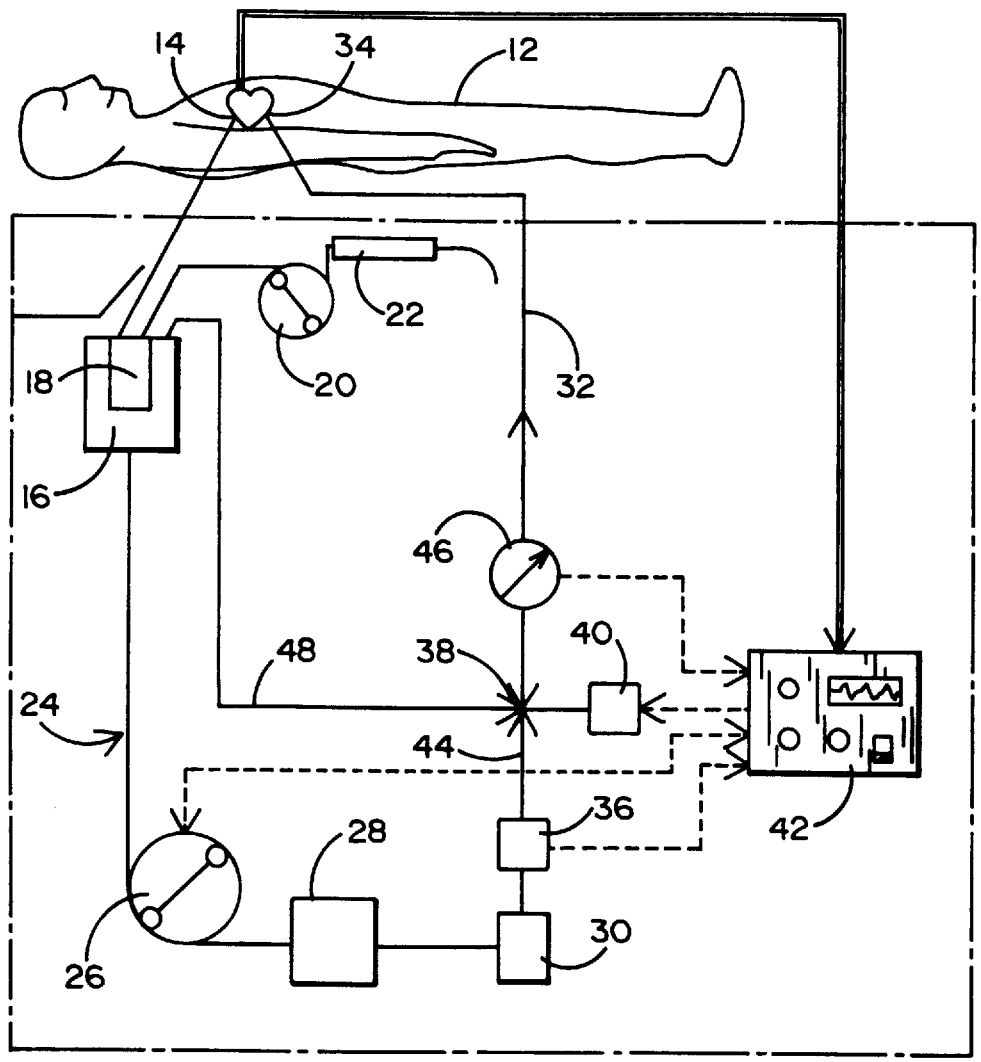
FIG. 1 is a schematic view of a heart-lung machine using the invention.

FIG. 1 shows the heart-lung machine 10 of this invention connected to a patient 12. During surgery, blood is diverted from the patient's vena cava 14 and conveyed to a venous reservoir 16. The reservoir 16 may conventionally contain a cardiotomy filter 18 through which blood scavenged from the surgery field by the cardiotomy pump 20 and sucker 22 can be returned to the cardiopulmonary bypass circuit 24.

In the cardiopulmonary circuit 24, blood taken from the reservoir 16 is continously pumped by the arterial pump 26 through the blood oxygenator 28 and the arterial filter 30. In conventional heart-lung machines, the output of arterial filter 30 is discharged directly into the arterial supply line 32 which returns the oxygenated blood to the aorta 34 of patient 12.

In accordance with the invention, however, the output of arterial filter 30 is preferably conveyed through an air-in-line detector 36 to a proportioning valve 38 operated by a pneumatic or electric actuator 40 under the control of a controller 42. The proportioning valve directs varying proportions of the blood flow from line 44 into the arterial supply line 32 through an averaging flow meter 46, and into the recycle line 48 as determined by the actuator 40. The recycle line 48 discharges recycled blood into the cardiopulmonary circuit 24 upstream from the arterial pump 26, and preferably into the venous reservoir 16 for reasons discussed below.

Figure 2:
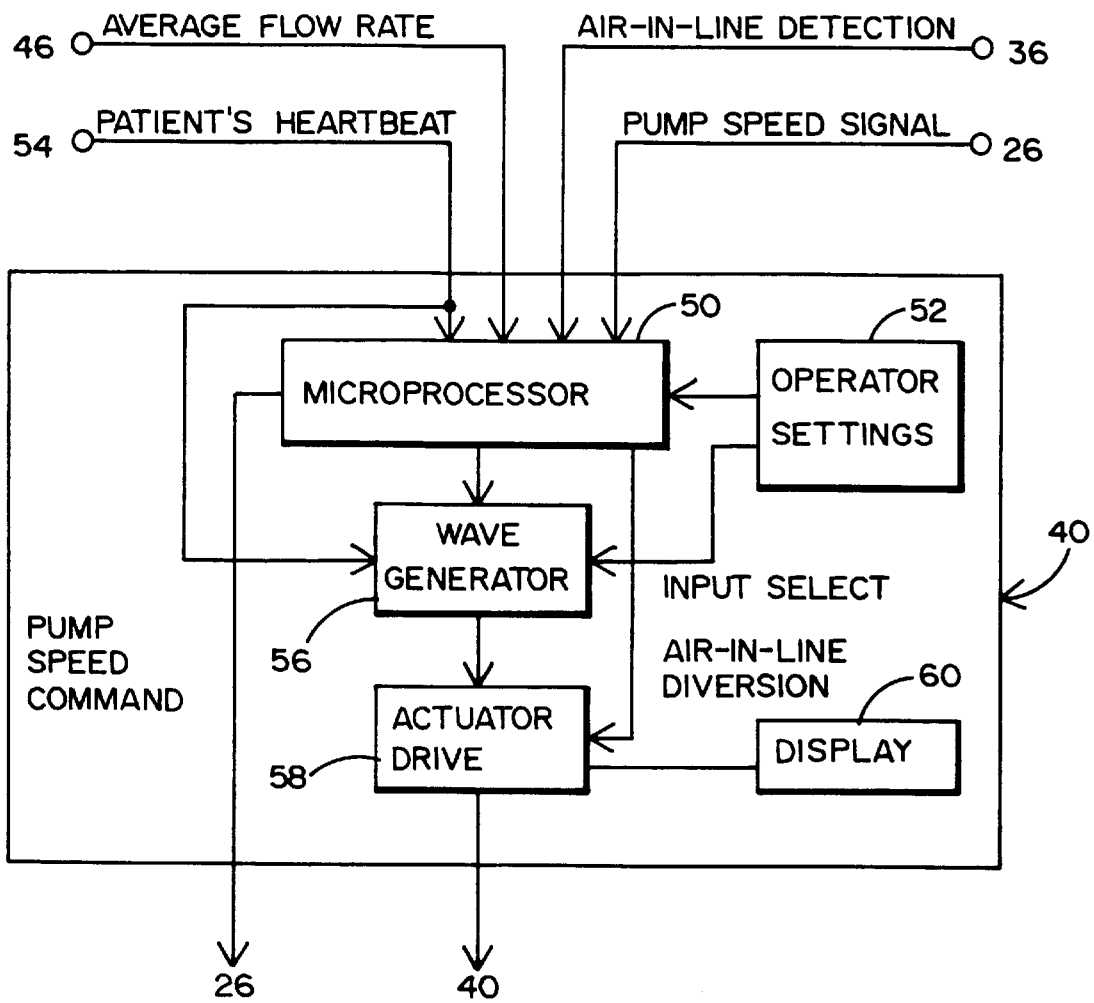
FIG. 2 is a block diagram of the controller of FIG. 1.

The operation of controller 42 is shown in more detail in FIG. 2. In that figure, the controller 40 is shown to contain a microprocessor 50 which is under the control of predetermined operator settings 52, and which receives input signals representative of the average flow rate in the arterial supply line 32 as measured by the averaging flow meter 46; the actual speed of arterial pump 26; and any air in line 44 detected by air-in-line detector 36. If desired, a further input signal representative of the actual beat of the heart 54 of patient 12 may also be supplied to the microprocessor 50.

A wave generator 56 is provided to produce a waveform simulating the natural beat of the patient's heart 54, either from digital data generated by the microprocessor during surgery (either on its own or from pre-surgical data received from heart 54), or, at the direction of the operator, in synchronism with the patient's actual heartbeat after the heart 54 has been restarted following surgery.

The output of wave generator 56 is applied to the pneumatic or electric actuator drive 58 which controls the actuator 40 of the proportioning valve 38. The wave input to actuator drive 58 may be momentarily overriden by an air-in-line signal from microprocessor 50 when an air bubble is detected in line 44 by the air-in-line detector 36. In that case, the microprocessor 50, knowing the speed of pump 26 and the length of the line 44 between the air-in-line detector 36 and the proportioning valve 38, can switch the actuator drive 58 to 100% recycle at the right moment and just long enough to divert the air bubble into recycle line 48 without significantly affecting the blood output into arterial supply line 32.

The microprocessor 50 also controls the speed of pump 26 as necessary to maintain the average flow rate measured by the flow rate meter 46 at the level set by the operator at 52. For monitoring purposes, the output of actuator drive 58 may be displayed on a display 60.

The output of recycle line 48 may be fed into the input of the arterial pump 26 or into the venous reservoir 16. The latter is preferable because it helps to prevent stagnation by increasing the turnover in the reservoir 16. In addition, if air bubbles in the line 44 are automatically diverted into the recycle line 48 as described above, discharge of the recycle line 48 into the reservoir 16 allows the air bubbles to be vented to atmosphere.

It is understood that the exemplary cardiopulmonary bypass circuit described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A heart-lung machine, comprising:
   a) a venous reservoir for receiving venous blood from a patient;
   b) an arterial supply line for conveying oxygenated blood to said patient;
   c) a cardiopulmonary circuit including said reservoir, said arterial supply line, and an arterial pump and an oxygenator interposed between said reservoir and said arterial supply line in said circuit;
   d) a recycle line connected to discharge blood into said circuit upstream of said pump; and
   e) a proportioning valve interposed in said circuit downstream of said pump and upstream of said arterial supply line and recycle line, said valve being arranged to convey selected varying proportions of the blood pumped by said arterial pump to said arterial supply line and lo said recycle line.

2. The heart-lung machine of claim 1, in which said valve is connected between said oxygenator and said arterial supply line.

3. The heart-lung machine of claim 2, in which an air-in-line detector is interposed in said circuit upstream of said valve.

4. The heart-lung machine of claim 2, in which an averaging flow meter is interposed in said circuit between said valve and said arterial supply line.

5. The heart-lung machine of claim 1, in which said recycle line is connected to discharge blood into said reservoir.

6. The heart-lung machine of claim 1, in which said proportioning valve is a diaphragm valve.

7. The heart-lung machine of claim 1, further comprising a controller operatively connected to said porportioning valve and arranged to vary said proportions in accordance with a predetermined waveform substantially simulating the waveform of a human heartbeat.

8. The heart-lung machine of claim 7, in which said arterial pump is operable at variable speeds, and in which said controller is further arranged to control the speed of said arterial pump in such a manner as to maintain a predetermined average blood flow rate in said arterial supply line.

9. The heart-lung machine of claim 7, in which an air-in-line detector is interposed in said circuit upstream of said valve, and said controller is further arranged to switch said valve to 100% recycle when a detected air bubble reaches said valve.

10. The heart-lung machine of claim 7, in which said patient has a natural heartbeat, and in which said controller is further arranged to either selectably generate a waveform for varying said proportions, or to vary said proportions in substantial synchronism with said heartbeat of said patient.

* * * * *